US006268367B1

(12) United States Patent
Piggott

(10) Patent No.: US 6,268,367 B1
(45) Date of Patent: Jul. 31, 2001

(54) PIPERAZINE DERIVATIVES FOR TREATING BONE DEFICIT CONDITIONS

(75) Inventor: James R. Piggott, Bothell, WA (US)

(73) Assignee: Zymogenetics, Inc., Seattle, WA (US)

( * ) Notice: Subject to any disclaimer, the term of this patent is extended or adjusted under 35 U.S.C. 154(b) by 0 days.

(21) Appl. No.: 09/027,570

(22) Filed: Feb. 23, 1998

(51) Int. Cl.$^7$ .......................... A61K 31/50; A61K 31/495
(52) U.S. Cl. ............................................. 514/252; 514/255
(58) Field of Search ................................. 514/227.8, 252, 514/255

(56) References Cited

U.S. PATENT DOCUMENTS 5,384,319 * 1/1995 Ferrini ................................ 514/227.8

FOREIGN PATENT DOCUMENTS

| 557030 | 10/1957 | (BE) . |
|---|---|---|
| 888139 | 7/1981 | (BE) . |
| 0 028 031 | 5/1981 | (EP) . |
| 0 318 235 | 5/1989 | (EP) . |
| 0 395 093 | 10/1990 | (EP) . |
| 0 436 734 | 7/1991 | (EP) . |
| 0 617 027 | 9/1994 | (EP) . |
| 0 733 627 | 9/1996 | (EP) . |
| 1031571 | 6/1953 | (FR) . |
| 832436 | 11/1960 | (FR) . |
| 1297718 | 11/1962 | (FR) . |
| 1303080 | 1/1963 | (FR) . |
| 2113942 | 6/1972 | (FR) . |
| 2291757 | 6/1976 | (FR) . |
| 2353540 | 12/1977 | (FR) . |
| 2377377 | 8/1978 | (FR) . |
| 874096 | 8/1961 | (GB) . |
| WO 98/37077 | 8/1998 | (WO) . |

OTHER PUBLICATIONS

Pastoureau et al., *J. Bone Miner. Res. 9* (*Suppl. 1*): S350, 1995.
Sabatini et al., *J. Bone Miner. Res. 9* (*Suppl. 1*): S199, 1995.
Valentijn et al., *Bone 21*: 269–274, 1997.
Farley et al., *Calcif. Tissue Int. 45*: 214–221, 1989.
Devogelaer et al., *Bone 18*: 141–150, 1996.
Bain et al., *J. Bone Min. Res. 8*: 435–442, 1993.
Vignery et al., *Bone 18*: 331–335, 1996.

* cited by examiner

*Primary Examiner*—Theodore J. Criares
(74) *Attorney, Agent, or Firm*—Townsend & Townsend & Crew LLP

(57) ABSTRACT

Piperazine derivatives useful in treating osteoporosis, bone fracture or deficiency, primary or secondary hyperparathyroidism, periodontal disease or defect, metastatic bone disorder, osteolytic bone disease, post-plastic surgery, post-prosthetic joint surgery and post-dental implantation.

13 Claims, No Drawings

PIPERAZINE DERIVATIVES FOR TREATING BONE DEFICIT CONDITIONS

BACKGROUND OF THE INVENTION

Bone is not a static tissue. It is subject to constant breakdown and resynthesis in a complex process mediated by osteoblasts, which produce new bone, and osteoclasts, which destroy bone. The activities of these cells are regulated by a large number of cytokines and growth factors, many of which have now been identified and cloned. Mundy has described the current knowledge related to these factors (Mundy, *Clin. Orthop.* 324:24–28, 1996; Mundy, *J. Bone Miner. Res.* 8:S505–10, 1993).

Although there is a great deal of information available on the factors which influence the breakdown and resorption of bone, information on growth factors which stimulate the formation of new bone is more limited. Investigators have searched for sources of such activities, and have found that bone tissue itself is a storehouse for factors which have the capacity for stimulating bone cells. Thus, extracts of bovine bone tissue obtained from slaughterhouses contain not only structural proteins which are responsible for maintaining the structural integrity of bone, but also biologically active bone growth factors which can stimulate bone cells to proliferate. Among these latter factors are transforming growth factor β, the heparin-binding growth factors (acidic and basic fibroblast growth factor), the insulin-like growth factors (insulin-like growth factor I and insulin-like growth factor II), and a recently described family of proteins called bone morphogenetic proteins (BMPs). All of these growth factors have effects on other types of cells, as well as on bone cells.

The BMPs are novel factors in the extended transforming growth factor β superfamily. They were first identified by Wozney J. et al. *Science* 242:1528–34, 1980, using gene cloning techniques, following earlier descriptions characterizing the biological activity in extracts of demineralized bone (Urist, *Science* 150:893–99, 1965). Recombinant BMP2 and BMP4 can induce new bone formation when they are injected locally into the subcutaneous tissues of rats (Wozney, *Molec. Reprod. Dev.* 32:160–67, 1992). These factors are expressed by normal osteoblasts as they differentiate, and have been shown to stimulate osteoblast differentiation and bone nodule formation in vitro as well as bone formation in vivo (Harris et al., *J. Bone. Miner. Res.* 9:855–63, 1994). This latter property suggests potential usefulness as therapeutic agents in diseases which result in bone loss.

The cells which are responsible for forming bone are osteoblasts. As osteoblasts differentiate from precursors to mature bone-forming cells, they express and secrete a number of enzymes and structural proteins of the bone matrix, including Type-1 collagen, osteocalcin, osteopontin and alkaline phosphatase (Stein G. et al. *Curr. Olpin. Cell Biol.* 2:1018–27, 1990; Harris S. et al. (1994), supra). They also synthesize a number of growth regulatory peptides which are stored in the bone matrix, and are presumably responsible for normal bone formation. These growth regulatory peptides include the BMPs (Harris et al. 1994), supra). In studies of primary cultures of fetal rat calvarial osteoblasts, BMPs 1, 2, 3, 4, and 6 are expressed by cultured cells prior to the formation of mineralized bone nodules (Harris et al. (1994), supra). Like alkaline phosphatase, osteocalcin and osteopontin, the BMPs are expressed by cultured osteoblasts as they proliferate and differentiate.

Although the BMPs are potent stimulators of bone formation in vitro and in vivo, there are disadvantages to their use as therapeutic agents to enhance bone healing. Receptors for the bone morphogenetic proteins have been identified in many tissues, and the BMPs themselves are expressed in a large variety of tissues in specific temporal and spatial patterns. This suggests that BMPs may have effects on many tissues other than bone, potentially limiting their usefulness as therapeutic agents when administered systemically. Moreover, since they are peptides, they would have to be administered by injection. These disadvantages impose severe limitations to the development of BMPs as therapeutic agents.

There is a plethora of conditions which are characterized by the need to enhance bone formation. Perhaps the most obvious is the case of bone fractures, where it would be desirable to stimulate bone growth and to hasten and complete bone repair. Agents that enhance bone formation would also be useful in facial reconstruction procedures. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis. In addition, or alternatively, the compounds of the present invention may modulate metabolism, proliferation and/or differentiation of normal or aberrant cells or tissues.

There are currently no satisfactory pharmaceutical approaches to managing any of these conditions. Bone fractures are still treated exclusively using casts, braces, anchoring devices and other strictly mechanical means. Further bone deterioration associated with post-menopausal osteoporosis has been decreased or prevented with estrogens or bisphosphonates.

U.S. Pat. Nos. 5,703,074, 5,670,535 and 5,061,704 disclose thiophene compounds which therapeutic value in bone metabolism. These thiophene compounds are useful in pathologies characterized by a loss of bone tissue such as osteoporosis, Paget's disease, periodontitis and rheumatoid arthritis. Some were found to stimulate bone formation as well, in particular, N-(3,3-dimethyl 5-(5-(3-p-tolylpropyl)thiophen-2-yl)pentyl)N'-(2,3,4-thrmethoxybenzyl)piperazine (Sabatini et al. (*J. Bone Miner. Res.* 9 (Suppl 1):S350, 1995).

The invention relates to methods for use in limiting undesired bone loss in a vertebrate at risk of such bone loss, in treating conditions that are characterized by undesired bone loss or by the need for bone growth, in treating fractures, and in treating cartilage disorders. Thus, the invention is directed to methods to treat bone disorders using the compounds described and to pharmaceutical compositions for this use.

SUMMARY OF THE INVENTION

The invention provides a method to enhance bone formation in a vertebrate animal which method comprises administering to a vertebrate subject in need of such treatment an amount of a compound of formula I:

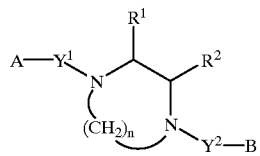

(I)

wherein A and B are each members independently selected from the group consisting of aryl, substituted aryl, carbocyclic ring, substituted carbocyclic ring, heterocyclic ring, substituted heterocyclic ring, and combinations thereof, said combinations being fused or covalently linked and said substituents being selected from the group consisting of halogen, haloalkyl, hydroxy, aryloxy, benzyloxy, alkoxy, haloalkoxy, amino, monoalkylamino, dialkylamino, acyloxy, acyl, alkyl and aryl; $R^1$ and $R^2$ are each independently selected from the group consisting of hydrogen and alkyl groups having from 1 to 6 carbon atoms, or taken together form a ring selected from the group consisting of saturated or unsaturated five-member rings, saturated or unsaturated six-member rings and saturated or unsaturated seven-member rings; $Y^1$ and $Y^2$ are each independently a bond or a divalent radical selected from the group consisting of —CH$_2$—, —NHC(O)—, —NRC(O)—, —NHC(S)—, —NRC(S)—, —NHC(=NH)—, —OC(O)—, —C(O)—, and —C(S)—, in which R is a lower alkyl group of from one to six carbon atoms; and n is an integer of from zero to four.

Within a related embodiments the compound has the formula:

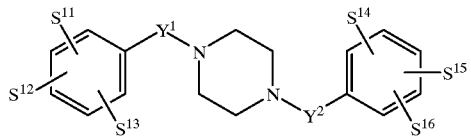

wherein, $Y^1$ and $Y^2$ are each independently a divalent radical selected from the group consisting of —CH$_2$—, —NHC(O)—, —NRC(O)—, —NHC(S)—, —NRC(S)—, —NHC(=NH)—, —OC(O)—, —C(O)—, or —C(S)—, in which R is a lower alkyl group of from one to six carbon atoms; and $S^{11}$, $S^{12}$, $S^{13}$, $S^{14}$, $S^{15}$, and $S^{16}$ are each independently a member selected from the group consisting of hydrogen, halogen, haloalkyl, hydroxy, aryloxy, benzyloxy, alkoxy, haloalkoxy, amino, monoalkylamino, dialkylamino, acyloxy, acyl, alkyl and aryl.

$Y^1$ is —NHC(O) or —CH$_2$—, $Y^2$ is —CH$_2$—, and $S^{11}$, $S^{12}$, $S^{13}$, $S^{14}$, $S^{15}$ and $S^{16}$ are each independently members selected from the group consisting of hydrogen, halogen, haloalkyl, hydroxy, alkoxy, haloalkoxy, amino, monoalkylamino or dialkylamino.

$S^{11}$, $S^{12}$, $S^{13}$, $S^{14}$, $S^{15}$, and $S^{16}$ are each independently members selected from the group consisting of hydrogen, halogen, trifluoromethyl, hydroxy and methoxy.

$Y^1$ is —NHC(O) or —CH$_2$—, $Y^2$ is —CH$_2$—, and $S^{11}$, $S^{12}$, $S^{13}$, $S^{14}$, $S^{15}$, and $S^{16}$ are each independently members selected from the group consisting of hydrogen, halogen, trifluoromethyl, hydroxy and methoxy.

Within other embodiments, the subject is characterized by a condition selected from the group consisting of osteoporosis, bone fracture or deficiency, primary or secondary hyperparathyroidism, periodontal disease or defect, metastatic bone disease, osteolytic bone disease, post-plastic surgery, post-prosthetic joint surgery, and post-dental implantation.

Within a related embodiment, one or more agents that promote bone growth or that inhibit bone resorption are administered to the subject. The agents are selected from the group consisting of bone morphogenic factors, osteogenic factors, cartilage-derived morphogenic proteins, growth hormones, and differentiating factors.

Within another aspect, the invention provides a pharmaceutical composition to enhance bone formation in a vertebrate animal which composition comprises a pharmaceutically acceptable excipient and an amount, effective to promote bone formation, of a compound of the formula:

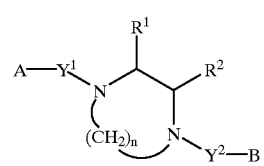

(I)

wherein

A and B are each members independently selected from the group consisting of aryl, substituted aryl, carbocyclic ring, substituted carbocyclic ring, heterocyclic ring, substituted heterocyclic ring, and combinations thereof, said combinations being fused or covalently linked and said substituents being selected from the group consisting of halogen, haloalkyl, hydroxy, aryloxy, benzyloxy, alkoxy, haloalkoxy, amino, monoalkylamino, dialkylamino, acyloxy, acyl, alkyl and aryl; $R^1$ and $R^2$ are each independently selected from the group consisting of hydrogen and alkyl groups having from 1 to 6 carbon atoms, or taken together form a ring selected from the group consisting of saturated or unsaturated five-member rings, saturated or unsaturated six-member rings and saturated or unsaturated seven-member rings; $Y^1$ and $Y^2$ are each independently a bond or a divalent radical selected from the group consisting of —CH$_2$—, —NHC(O)—, —NRC(O)—, —NHC(S)—, —NRC(S)—, —NHC(=NH)—, —OC(O)—, —C(O)—, and —C(S)—, in which R is a lower alkyl group of from one to six carbon atoms; and n is an integer of from zero to four.

Within related embodiments the compound has the formula:

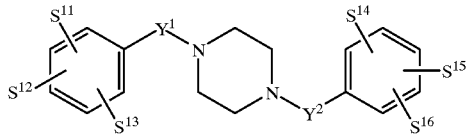

wherein, $Y^1$ and $Y^2$ are each independently a divalent radical selected from the group consisting of —CH$_2$—, —NHC(O)—, —NRC(O)—, —NHC(S)—, —NRC(S)—, —NHC(=NH)—, —OC(O)—, —C(O)—, or —C(S)—, in which R is a lower alkyl group of from one to six carbon atoms; and $S^{11}$, $S^{12}$, $S^{13}$, $S^{14}$, $S^{15}$, and $S^{16}$ are each independently a member selected from the group consisting of hydrogen, halogen, haloalkyl, hydroxy, aryloxy, benzyloxy, alkoxy, haloalkoxy, amino, monoalkylamino, dialkylamino, acyloxy, acyl, alkyl and aryl.

$Y^1$ is —NHC(O) or —CH$_2$—, $Y^2$ is —CH$_2$—, and $S^{11}$, $S^{12}$, $S^{13}$, $S^{14}$, $S^{15}$ and $S^{16}$ are each independently members selected from the group consisting of hydrogen, halogen, haloalkyl, hydroxy, alkoxy, haloalkoxy, amino, monoalkylamino or dialkylamino. $S^{11}$, $S^{12}$, $S^{13}$, $S^{14}$, $S^{15}$, and $S^{16}$ are each independently members selected from the group consisting of hydrogen, halogen, trifluoromethyl, hydroxy and methoxy.

$Y^1$ is —NHC(O) or —$CH_2$—, $Y^2$ is —$CH_2$—, and $S^{11}$, $S^{12}$, $S^{13}$, $S^{14}$, $S^{15}$, and $S^{16}$ are each independently members selected from the group consisting of hydrogen, halogen, trifluoromethyl, hydroxy and methoxy.

These and other aspects of the invention will become evident upon reference to the following detailed description.

DETAILED DESCRIPTION OF THE INVENTION

All references cited herein are incorporated in their entirety by reference.

The compounds of the present invention were initially identified in a high through-put screen for compounds with the ability to mimic the effects generated by calcitonin's interaction with its receptor and, by such interaction, stimulate G-protein-mediated activation by adenyl cyclase. Such mimetic compounds are useful for inhibition of bone resorption. Calcitonin, a peptide hormone secreted by the thyroid and thymus of mammals, plays an important role in maintaining bone homeostasis. Calcitonin inhibits bone resorption through binding and activation of a specific calcitonin receptor on osteoclasts with a resultant decrease in the amount of calcium released by bone into the extracellular fluid (The Calcitonins—Physiology and Pharmacology, Azria (ed.), Karger, Basel, Su., 1989). The identified piperazine derivatives inhibited bone resorption. Further analysis described herein indicated a bone forming activity as well. The anti-resorptive heterocyclic compound described by Sabatini et al., (1995) supra, also had bone-forming activities. Estrogen has been reported to be have anabolic properties in addition to anti-resorptive activity (Bain et al, *J. Bone Miner. Res.* 8:435–42, 1993). Anecdotally, bisphosphonates are claimed to have both anti-resorptive and anabolic or bone-forming activity in humans (Devogalaer et al., *Bone* 18: 141–50, 1996) and calcitonin has been claimed to have an anabolic effect on bone (Farley et al., *Calcif. Tissue Int.* 50:67–73, 1992 and Wallach et al., *Calcif. Tissue Int.* 52:335–39, 1993). It is likely that resorption inhibitors may appear to have bone forming activity since bone formation continues for a period of time after resorption stops.

As used herein, "limit" or "limiting" and "treat" or "treatment" are interchangeable terms. The terms include a postponement of development of bone deficit symptoms and/or a reduction in the severity of such symptoms that will or are expected to develop. The terms further include ameliorating existing bone or cartilage deficit symptoms, preventing additional symptoms, ameliorating or preventing the underlying metabolic causes of symptoms, and/or encouraging bone growth. Thus, the terms denote that a beneficial result has been conferred on a vertebrate subject with a cartilage, bone or skeletal deficit, or with the potential to develop such deficit.

By "bone deficit" is meant an imbalance in the ratio of bone formation to bone resorption, such that, if unmodified, the subject will exhibit less bone than desirable, or the subject's bones will be less intact and coherent than desired. Bone deficit may also result from fracture, from surgical intervention or from dental or periodontal disease. By "cartilage defect" is meant damaged cartilage, less cartilage than desired, or cartilage that is less intact and coherent than desired.

Representative uses of the compounds of the present invention include: repair of bone defects and deficiencies, such as those occurring in closed, open and non-union fractures; prophylactic use in closed and open fracture reduction; promotion of bone healing in plastic surgery; stimulation of bone ingrowth into non-cemented prosthetic joints and dental implants; elevation of peak bone mass in pre-menopausal women; treatment of growth deficiencies; treatment of periodontal disease and defects, and other tooth repair processes; increase in bone formation during distraction osteogenesis; and treatment of other skeletal disorders, such as age-related osteoporosis, post-menopausal osteoporosis, glucocorticoid-induced osteoporosis, diabetes-associated osteoporosis or disuse osteoporosis and arthritis. The compounds of the present invention can also be useful in repair of congenital, trauma-induced or surgical resection of bone (for instance, for cancer treatment), and in cosmetic surgery. Further, the compounds of the present invention can be used for limiting or treating cartilage defects or disorders, and may be useful in wound healing or tissue repair. A key indication for compounds having a dual functionality of anti-resorption and bone formation would be to promote bone maintenance and resorption during the menopausal process.

Bone or cartilage deficit or defect can be treated in vertebrate subjects by administering compounds of the invention which exhibit certain structural and functional characteristics. The compositions of the invention may be administered systemically or locally. For systemic use, the compounds herein are formulated for parenteral (e.g., intravenous, subcutaneous, intramuscular, intraperitoneal, intranasal or transdermal) or enteral (e.g., oral or rectal) delivery according to conventional methods. Intravenous administration can be by a series of injections or by continuous infusion over an extended period. Administration by injection or other routes of discretely spaced administration can be performed at intervals ranging from weekly to once to three times daily. Alternatively, the compounds disclosed herein may be administered in a cyclical manner (administration of disclosed compound; followed by no administration; followed by administration of disclosed compound, and the like). Treatment will continue until the desired outcome is achieved. In general, pharmaceutical formulations will include a compound of the present invention in combination with a pharmaceutically acceptable vehicle, such as saline, buffered saline, 5% dextrose in water, borate-buffered saline containing trace metals or the like. Formulations may further include one or more excipients, preservatives, solubilizers, buffering agents, albumin to prevent protein loss on vial surfaces, lubricants, fillers, stabilizers, etc. Methods of formulation are well known in the art and are disclosed, for example, in Remington: *The Science and Practice of Pharmacy*, Gennaro, ed., Mack Publishing Co., Easton, Pa., 19th ed., 1995. Pharmaceutical compositions for use within the present invention can be in the form of sterile, non-pyrogenic liquid solutions or suspensions, coated capsules, suppositories, lyophilized powders, transdermal patches or other forms known in the art. Local administration may be by injection at the site of injury or defect, or by insertion or attachment of a solid carrier at the site, or by direct, topical application of a viscous liquid, or the like. For local administration, the delivery vehicle preferably provides a matrix for the growing bone or cartilage, and more preferably is a vehicle that can be absorbed by the subject without adverse effects.

Delivery of compounds herein to wound sites may be enhanced by the use of controlled-release compositions, such as those described in WIPO publication WO 93/20859. Films of this type are particularly useful as coatings for prosthetic devices and surgical implants. The films may, for example, be wrapped around the outer surfaces of surgical screws, rods, pins, plates and the like. Implantable devices of this type are routinely used in orthopedic surgery. The films can also be used to coat bone filling materials, such as hydroxyapatite blocks, demineralized bone matrix plugs, collagen matrices and the like. In general, a film or device as described herein is applied to the bone at the fracture site. Application is generally by implantation into the bone or attachment to the surface using standard surgical procedures.

In addition to the copolymers and carriers noted above, the biodegradable films and matrices may include other active or inert components. Of particular interest are those agents that promote tissue growth or infiltration, such as growth factors. Exemplary growth factors for this purpose include epidermal growth factor (EGF), fibroblast growth factor (FGF), platelet-derived growth factor (PDGF), transforming growth factors (TGFs), parathyroid hormone (PTH), leukemia inhibitory factor (LIF), and insulin-like growth factors (IGFs) and the like. Agents that promote bone growth, such as bone morphogenetic proteins (WIPO publication WO 90/11366), osteogenin (Sampath et al., *Proc. Natl. Acad. Sci. USA* 84:7109–13, 1987) and NaF (Tencer et al. *J. Biomed. Mat. Res.* 23: 571–89, 1989) are also preferred. Biodegradable films or matrices include calcium sulfate, tricalcium phosphate, hydroxyapatite, polylactic acid, polyanhydrides, bone or dermal collagen, pure proteins, extracellular matrix components and the like and combinations thereof. Such biodegradable materials may be used in combination with non-biodegradable materials, to provide desired mechanical, cosmetic or tissue or matrix interface properties.

Alternative methods for delivery of compounds of the present invention include use of ALZET osmotic minipumps (Alza Corp., Palo Alto, Calif.); sustained release matrix materials such as those disclosed in Wang et al. (WIPO publication WO 90/11366); electrically charged dextran beads, as disclosed in Bao et al. (WIPO publication WO 92/03125); collagen-based delivery systems, for example, as disclosed in Ksander et al., *Ann. Surq.* 211:288–94, 1990; methylcellulose gel systems, as disclosed in Beck et al., *J. Bone Min. Res.* 6:1257-65, 1991; and alginate-based systems, as disclosed in Edelman et al., *Biomaterials* 12:619–26, 1991 and the like. Other methods well known in the art for sustained local delivery in bone include porous coated metal prostheses that can be impregnated and solid plastic rods with therapeutic compositions incorporated within them.

In additional formulations, conventional preparations such as those described below may be used.

Aqueous suspensions may contain the active ingredient in admixture with pharmacologically acceptable excipients, comprising suspending agents, such as methyl cellulose; and wetting agents, such as lecithin, lysolecithin or long-chain fatty alcohols. The said aqueous suspensions may also contain preservatives, coloring agents, flavoring agents and sweetening agents in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

If desired, the osteogenic agents can be incorporated into liposomes by any of the reported methods of preparing liposomes for use in treating various pathogenic conditions. The present compositions may utilize the compounds noted above incorporated in liposomes in order to direct these compounds to macrophages, monocytes, other cells and tissues and organs which take up the liposomal composition. The liposome-incorporated compounds of the invention can be utilized by parenteral administration, to allow for the efficacious use of lower doses of the compounds. Ligands may also be incorporated to further focus the specificity of the liposomes.

Suitable conventional methods of liposome preparation include, but are not limited to, those disclosed by Bangham, et al., *J. Mol. Biol.* 23:238–52, 1965, Olson, et al., *Biochim. Bionhys. Acta* 557:9–23, 1979, Szoka, et al., *Proc. Natl. Acad. Sci. USA* 75:4194–8, 1978, Mayhew, et al., *Biochim Biophys Acta* 775:169–74, 1984, Kim, et al., *Biochim Biophys Acta* 728:339–48, 1983 and Mayer, et al., *Biochim Biophys Acta* 858:161–8, 1986.

The liposomes may be made from the present compounds in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol. Synthetic phospholipids that may also be used, include, but are not limited to: dimyristoylphosphatidylcholine, dioleoylphosphatidylcholine, dipalmitoylphosphatidylcholine and distearoylphosphatidycholine, and the corresponding synthetic phosphatidylethanolamines and phosphatidylglycerols. Cholesterol or other sterols, cholesterol hemisuccinate, glycolipids, cerebrosides, fatty acids, gangliosides, sphingolipids, 1,2-bis(oleoyloxy)-3-(trimethylammonio)propane (DOTAP), N-[1-(2,3-dioleoyl)propyl-N,N,N-trimethylammonium chloride (DOTMA), and other cationic lipids may be incorporated into the liposomes, as is known to those skilled in the art. The relative amounts of phospholipid and additives used in the liposomes may be varied if desired. The preferred ranges are from about 60 to 90 mole percent of the phospholipid; cholesterol, cholesterol hemisuccinate, fatty acids or cationic lipids may be used in amounts ranging from 0 to 50 mole percent. The amounts of the present compounds incorporated into the lipid layer of liposomes can be varied with the concentration of the lipids ranging from about 0.01 to about 50 mole percent.

Using conventional methods, approximately 20 to 30% of the compound present in solution can be entrapped in liposomes; thus, approximately 70 to 80% of the active compound is wasted. In contrast, where the compound is incorporated into liposomes, virtually all of the compound is incorporated into the liposome, and essentially none of the active compound is wasted.

The liposomes with the above formulations may be made still more specific for their intended targets with the incorporation of monoclonal antibodies or other ligands specific for a target. For example, monoclonal antibodies to the BMP receptor may be incorporated into the liposome by linkage to phosphatidylethanolamine (PE) incorporated into the liposome by the method of Leserman, et al., *Nature* 288:602–4, 1980.

Veterinary uses of the disclosed compounds are also contemplated. Such uses would include limitation or treatment of bone or cartilage deficits or defects in domestic animals, livestock and thoroughbred horses. The compounds described herein can also modify a target tissue or organ environment, so as to attract bone-forming cells to an environment in need of such cells.

The compounds of the present invention may also be used to stimulate growth of bone-forming cells or their precursors, or to induce differentiation of bone-forming cell precursors, either in vitro or ex vivo. As used herein, the term "precursor cell" refers to a cell that is committed to a differentiation pathway, but that generally does not express markers or function as a mature, fully differentiated cell. As used herein, the term "mesenchymal cells" or "mesenchymal stem cells" refers to pluripotent progenitor cells that are capable of dividing many times, and whose progeny will give rise to skeletal tissues, including cartilage, bone, tendon, ligament, marrow stroma and connective tissue (see Caplan, *J. Orthop. Res.* 9:641–50, 1991). As used herein, the term "osteogenic cells" includes osteoblasts and osteoblast precursor cells. More particularly, the disclosed compounds are useful for stimulating a cell population containing marrow mesenchymal cells, thereby increasing the number of osteogenic cells in that cell population. In a preferred method, hematopoietic cells are removed from the cell population, either before or after stimulation with the disclosed compounds. Through practice of such methods, osteogenic cells may be expanded. The expanded osteogenic cells can be infused (or re-infused) into a vertebrate subject in need thereof. For instance, a subject's own mesenchymal stem cells can be exposed to compounds of the present invention ex vivo, and the resultant osteogenic cells could be infused or directed to a desired site within the subject, where further proliferation and/or differentiation of the osteogenic cells can occur without immunorejection. Alternatively, the cell population exposed to the disclosed compounds may be immortalized human fetal osteoblastic or osteogenic cells. If such cells are infused or implanted in a vertebrate subject, it may be advantageous to "immunoprotect" these non-self cells, or to immunosuppress (preferably locally) the recipient to enhance transplantation and bone or cartilage repair.

Within the present invention, an "effective amount" of a composition is that amount which produces a statistically significant effect. For example, an "effective amount" for therapeutic uses is the amount of the composition comprising an active compound herein required to provide a clinically significant increase in healing rates in fracture repair; reversal of bone loss in osteoporosis; reversal of cartilage defects or disorders; prevention or delay of onset of osteoporosis; stimulation and/or augmentation of bone formation in fracture non-unions and distraction osteogenesis; increase and/or acceleration of bone growth into prosthetic devices; and repair of dental defects. Such effective amounts will be determined using routine optimization techniques and are dependent on the particular condition to be treated, the condition of the patient, the route of administration, the formulation, and the judgment of the practitioner and other factors evident to those skilled in the art. The dosage required for the compounds of the invention (for example, in osteoporosis where an increase in bone formation is desired) is manifested as a statistically significant difference in bone mass between treatment and control groups. This difference in bone mass may be seen, for example, as a 5–20% or more increase in bone mass in the treatment group. Other measurements of clinically significant increases in healing may include, for example, tests for breaking strength and tension, breaking strength and torsion, 4-point bending, increased connectivity in bone biopsies and other biomechanical tests well known to those skilled in the art. General guidance for treatment regimens is obtained from experiments carried out in animal models of the disease of interest.

Auxiliary assays can be used as controls to determine other effects of test compounds. For example, mitogenic activity can be measured using screening assays featuring a serum-response element (SRE) as a promoter and a luciferase reporter gene. More specifically, these screening assays can detect signaling through SRE-mediated pathways, such as the protein kinase C pathway. For instance, an osteoblast activator SRE-luciferase screen and an insulin mimetic SRE-luciferase screen are useful for this purpose.

Compounds of the present invention can be further tested in intact animals using an in vivo, dosing assay. Prototypical dosing may be accomplished by subcutaneous, intraperitoneal or oral administration, and may be performed by injection, sustained release or other delivery techniques. The time period for administration of test compound may vary (for instance, 28 days as well as 35 days may be appropriate). An exemplary, in vivo subcutaneous dosing assay may be conducted as follows:

In a typical study, 70 three-month-old female Sprague-Dawley rats are weight-matched and divided into seven groups, with ten animals in each group. This includes a baseline control group of animals sacrificed at the initiation of the study; a control group administered vehicle only; a PBS-treated control group; and a positive control group administered a compound (non-protein or protein) known to promote bone growth. Three dosage levels of the compound to be tested are administered to the remaining three groups.

Briefly, test compound, positive control compound, PBS, or vehicle alone is administered subcutaneously once per day for 35 days. All animals are injected with calcein nine days and two days before sacrifice (two injections of calcein administered each designated day). Weekly body weights are determined. At the end of the 35-day cycle, the animals are weighed and bled by orbital or cardiac puncture. Serum calcium, phosphate, osteocalcin, and CBCs are determined. Both leg bones (femur and tibia) and lumbar vertebrae are removed, cleaned of adhering soft tissue, and stored in 70% ethanol for evaluation, as performed by peripheral quantitative computed tomography (pQCT; Ferretti, *Bone.* 17:353S–64S, 1995), dual energy X-ray absorptiometry (DEXA; Laval-Jeantet et al., *Calcif. Tissue Intl.* 56:14–18, 1995; Casez et al., *Bone and Mineral* 26:61–8,1994) and/or histomorphometry. The effect of test compounds on bone remodeling can thus be evaluated.

Lead compounds can also be tested in acute ovariectomized animals (prevention model) using an in vivo dosing assay. Such assays may also include an estrogen-treated group as a control. An exemplary subcutaneous dosing assay is performed as follows:

In a typical study, 80 three-month-old female Sprague-Dawley rats are weight-matched and divided into eight groups, with ten animals in each group. This includes a baseline control group of animals sacrificed at the initiation of the study; three control groups (sham ovariectomized (sham OVX)+vehicle only; ovariectomized (OVX)+vehicle only; PBS-treated OVX); and a control OVX group that is administered a compound known to promote bone growth. Three dosage levels of the compound to be tested are administered to the remaining three groups of OVX animals.

Since ovariectomy (OVX) induces hyperphagia, all OVX animals are pair-fed with sham OVX animals throughout the 35 day study. Briefly, test compound, positive control compound, PBS, or vehicle alone is administered subcutaneously once per day for 35 days. Alternatively, test compound can be formulated in implantable pellets that are implanted for 35 days, or may be administered orally, such as by gastric gavage. All animals, including sham OVX/vehicle and OVX/vehicle groups, are injected intraperitoneally with calcein nine days and two days before sacrifice (two injections of calcein administered each designated day, to ensure proper labeling of newly formed bone). Weekly body weights are determined. At the end of the 35-day cycle, the animals' blood and tissues are processed as described above.

Lead compounds may also be tested in chronic OVX animals (treatment model). An exemplary protocol for treatment of established bone loss in ovariectomized animals that can be used to assess efficacy of anabolic agents may be performed as follows. Briefly, 80 to 100 six month old female, Sprague-Dawley rats are subjected to sham surgery (sham OVX) or ovariectomy (OVX) at time 0, and 10 rats are sacrificed to serve as baseline controls. Body weights are recorded weekly during the experiment. After approximately 6 weeks or more of bone depletion (42 days), 10 sham OVX and 10 OVX rats are randomly selected for sacrifice as depletion period controls. Of the remaining animals, 10 sham OVX and 10 OVX rats are used as placebo-treated controls. The remaining OVX animals are treated with 3 to 5 doses of test drug for a period of 5 weeks (35 days). As a positive control, a group of OVX rats can be treated with an agent such as PTH, a known anabolic agent in this model (Kimmel et al., *Endocrinology* 132:1577–84, 1993). To determine effects on bone formation, the following procedure can be followed. The femurs, tibiae and lumbar vertebrae 1 to 4 are excised and collected. The proximal left and right tibiae are used for pQCT measurements, cancellous bone mineral density (BMD) (gravimetric determination), and histology, while the midshaft of each tibiae is subjected to cortical BMD or histology. The femurs are prepared for pQCT scanning of the midshaft prior to biomechanical testing. With respect to lumbar vertebrae (LV), LV2 are processed for BMD (pQCT may also be performed); LV3 are prepared for undecalcified bone histology; and LV4 are processed for mechanical testing.

The compounds useful in the methods of the invention are of the formula:

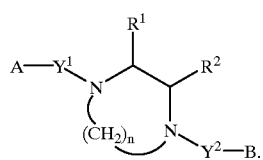

(I)

In this formula, the letters A and B each independently represent an aryl group, a substituted aryl group, a carbocyclic ring, a substituted carbocyclic ring, a heterocyclic ring, a substituted heterocyclic ring, or combinations thereof. The combinations can be fused or covalently linked. Examples of carbocyclic and heterocyclic groups include cyclohexyl, cyclohexenyl, piperazinyl, pyrazinyl, morpholinyl, imidazolyl, triazolyl and thiazolyl. As noted above, each of A and B can be an aryl group. The term "aryl" refers to an aromatic substituent which may be a single ring or multiple rings which are fused together, linked covalently or linked to a common group such as an ethylene or methylene moiety. The aromatic rings may each contain heteroatoms. Examples of aryl groups include phenyl, naphthyl, biphenyl, diphenylmethyl, 2,2-diphenyl-1-ethyl, thienyl, pyridyl and quinoxalyl. Additionally, the aryl groups may be attached to other parts of the molecule at any position on the aryl radical which would otherwise be occupied by a hydrogen atom (such as, for example, 2-pyridyl, 3-pyridyl and 4-pyridyl).

The aryl groups, along with any carbocyclic or heterocyclic groups may also be optionally substituted. The substituents are typically halogen, haloalkyl, hydroxy, aryloxy, benzyloxy, alkoxy, haloalkoxy, amino, monoalkylamino, dialkylamino, acyloxy, acyl, alkyl or additional aryl groups. The term "alkyl," as used herein, refers to a saturated hydrocarbon radical which may be straight-chain or branched-chain (for example, ethyl, isopropyl, or t-amyl), or cyclic (for example cyclobutyl, cyclopropyl or cyclopentyl). Preferred alkyl groups are those containing 1 to 6 carbon atoms. All numerical ranges in this specification and claims are intended to be inclusive of their upper and lower limits. The term "alkoxy" refers to an alkyl radical as described above which also bears an oxygen substituent which is capable of covalent attachment to another hydrocarbon radical (such as, for example, methoxy, ethoxy and t-butoxy).

The symbols $R^1$ and $R^2$ are each independently hydrogen or alkyl groups having from 1 to 6 carbon atoms. In some embodiments $R^1$ and $R^2$ can be joined together to form a ring which is a four-, five-, six- or seven-member ring, saturated or unsaturated. For those embodiments in which the ring is unsaturated, the ring can be an aromatic ring (e.g., phenyl or naphthyl) or a heteroaromatic ring (e.g., pyridyl, thienyl, imidazolyl).

The symbols $Y^1$ and $Y^2$ each independently represent a bond or a divalent radical which is —$CH_2$—, —NHC(O)—, —NRC(O)—, —NHC(S)—, —NRC(S)—, —NHC(=NH)—, —OC(O)—, —C(O)—, or —C(S)—, in which R is a lower alkyl group of from one to six carbon atoms. In preferred embodiments, $Y^2$ represents a divalent radical which is a carbonyl, thiocarbonyl or methylene, represented as —C(O)—, —C(S)— or —$CH_2$—, respectively. In other preferred embodiments, $Y^1$ is —NHC(O)—, —NRC(O)—, —C(O)—, or —C(S)—.

The letter n represents an integer of from zero to four.

In one group of preferred embodiments, the compounds are piperazine-based compounds which are represented by the formula:

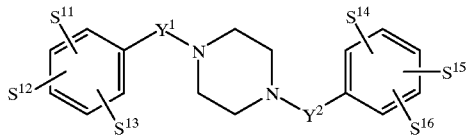

In this formula, the symbols $Y^1$ and $Y^2$ have the meaning provided above. The symbols $S^{11}$, $S^{12}$, $S^{13}$, $S^{14}$, $S^{15}$, and $S^{16}$ each independently represent a substituent on the attached aromatic ring which is hydrogen, halogen, haloalkyl, hydroxy, aryloxy, benzyloxy, alkoxy, haloalkoxy, amino, monoalkylamino, dialkylamino, acyloxy, acyl, alkyl and aryl. In particularly preferred embodiments, $Y^1$ is —NHC(O) or —$CH_2$—, $Y^2$ is —$CH_2$—, and $S^{11}$, $S^{12}$, $S^{13}$, $S^{14}$, $S^{15}$, and $S^{16}$ each independently represent hydrogen, halogen, haloalkyl, hydroxy, alkoxy, haloalkoxy, amino, monoalkylamino or dialkylamino. In certain preferred embodiments, at least one and preferably at least two of the substituents on each aromatic ring are other than hydrogen. Most preferably, the substituents are halogen, trifluoromethyl, hydroxy and methoxy.

The compounds used in the present invention can be prepared by standard synthetic methods which are known to those of skill in the art. A general synthetic scheme directed to piperazine derivatives is shown below. Thus, a monoprotected piperazine (e.g., t-BOC-piperazine) can be treated with an aryl isocyanate to provide a urea 1a. Removal of the protecting group from 1a provides 1b which can be alkylated or acylated according to conventional methods with, for example, a substituted benzyl halide or a substituted benzoyl chloride to provide 1c and 1d, respectively.

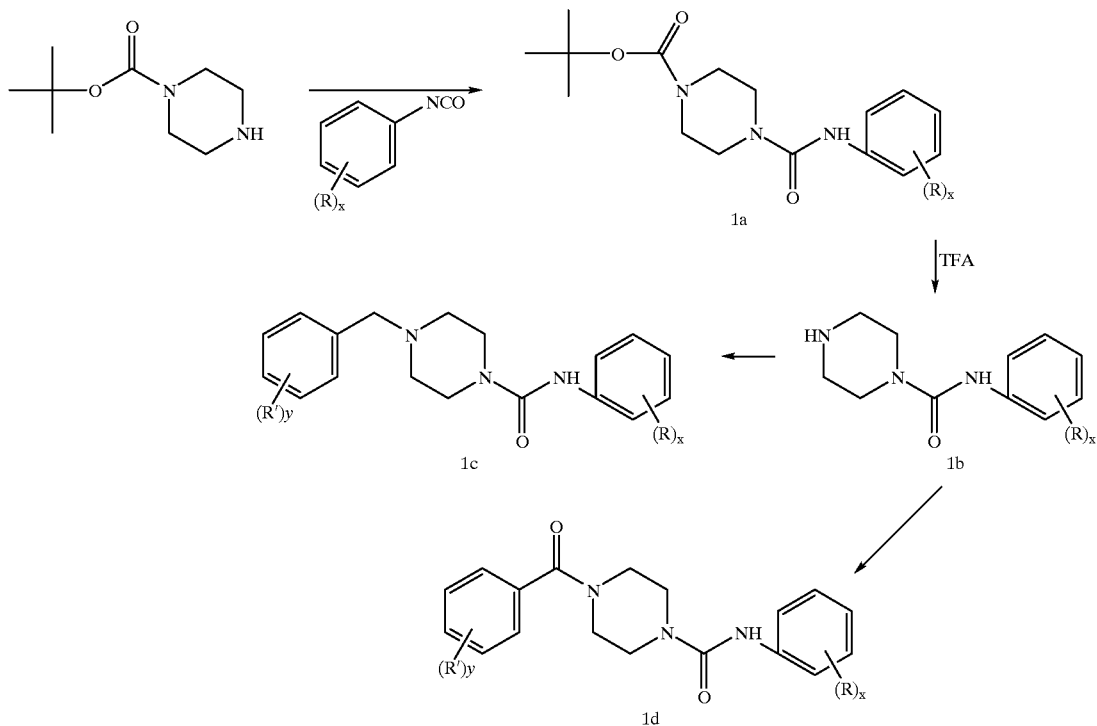

Alternatively, t-Boc piperazine can be alkylated using a reductive amination route as illustrated below. Following the reductive alkylation with, for example, an aromatic aldehyde, the protecting group can be removed and the remaining piperazine nitrogen can be acylated with an aryl or alkyl isocyanate.

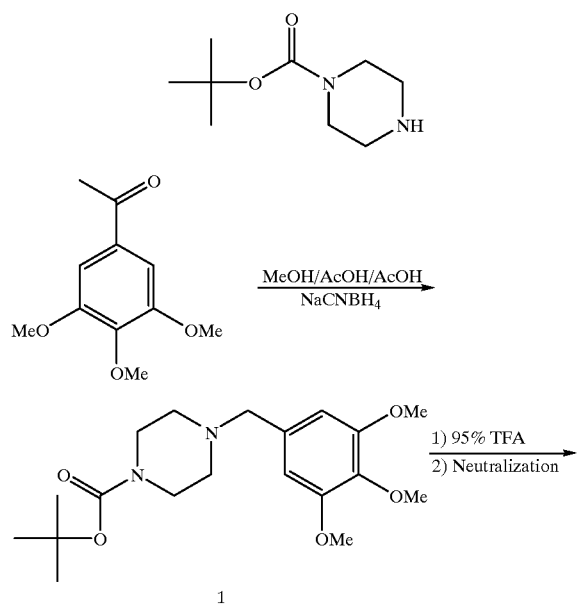

Still other preparative methods can be employed which are analogous to those described for the preparation of related compounds in U.S. Pat. Nos. 5,286,728 and 5,384,319.

In another synthetic methodology, a suitably substituted hydroxybenzaldehyde is first linked to a solid support, such as Wang resin. The free aldehyde group is then subjected to reductive alkylation employing a monoprotected diamine, such as BOC-piperazine. The protecting group is then removed and the resin-bound compound is acylated with a variety of reagents, such as carboxylic acids, isocyanates, isothiocyanates or sulfonyl halides. The mono-protected diamines, including piperazines, are either commercially available or can be prepared by a variety of methods known to those skilled in the art of organic synthesis. In one approach, 4-hydroxy-3-methoxybenzaldehyde is attached to Wang resin by Mitsonobu alkylation employing triphenylphosphine and diethylazodicarboxylate. The free aldehyde group of the resin-bound compound is then reductively alkylated with BOC-piperazine employing borane-pyridine complex. The BOC group is then selectively removed with 10% TFA/DCM and the free nitrogen is then acylated with arylisocyanates. Cleavage of the resulting compound is then effected by standard methods, for example using 50% TFA/DCM for 30 minutes. One of skill in the art will recognize that a number of alternative procedures exist for the preparation of the present compounds, including reversing the order of synthesis on the resin, using other reagents for the acylations and couplings which are described in, for example, March, *Advanced Organic Chemistry*, Fourth Edition, Wiley-Interscience, New York, 1992.

The foregoing description and the following examples are offered primarily for illustration and not as limitations. It will be readily apparent to those of ordinary skill in the art that the operating conditions, materials, procedural steps and other parameters of the system described herein may be further modified or substituted in various ways without departing from the spirit and scope of the invention. The invention is further illustrated by the following non-limiting examples.

EXAMPLES

Example 1

Synthesis of 50-0231

This example illustrates the synthesis 50-0231, from commercially available starting materials using the synthetic schemes as described above. Briefly, t-Boc-piperazine (8.6 g, 100 mmol) and vanillin acetate (100 mmol) are combined with anhydrous MeOH (150 mL) and stirred until a clear solution is obtained. Acetic acid (6.0 g) is added followed by 47 g of molecular sieves (4 Å). After gently stirring for 1 hr, the mixture is chilled in ice and NaCNBH$_4$ (6.1 g, 100 mmol) is added in small portions over a period of 1.5 hr with gentle stirring. Stirring is continued for 70 hr and the mixture is filtered and the filtrate is evaporated under reduced pressure. The resultant oily residue is treated with water and 10 g of NH$_4$Cl. The suspension is stirred and acidified to pH ~4 with solid KHSO$_4$. The suspension is neutralized with NaHCO$_3$ and extracted thoroughly with EtOAc. The organic layer is washed with water, dried over Na$_2$SO$_4$, and concentrated under reduced pressure to provide a semi-solid residue. The residue is titrated with anhydrous ether and the crystalline solid is filtered off and washed with cold ether. The solid is dried in air for 2 hr, then in vacuo for 2 hr.

A portion of the solid (20 mmol) is dissolved in chilled 95% TFA/H$_2$O (50 mL). The mixture is stirred for 30 minutes in ice, then TFA was removed under reduced pressure. The residue is treated with water, acidified with 1N HCl to pH 3–4, and extracted with ether (3×20 mL). The aqueous layer is chilled in ice and neutralized with solid Na$_2$CO$_3$ and the pH is adjusted to 10 with 1N NaOH. The resulting solution is extracted with EtOAc (5×40 mL). The aqueous layer is saturated with NaCl and again extracted with EtOAc (2×30 mL). The combined EtOAc extracts are washed with water, brine, dried over Na$_2$SO$_4$, filtered and evaporated under reduced pressure. The compound is dried overnight in a vacuum desiccator, dissolved in anhydrous DMF (35 mL) and chilled in ice. To the chilled stirring solution is added portion-wise a solution of 3-trifluoromethylisocyanate (3.74 g, 20 mmol) in dry DMF (15 mL). The reaction is monitored for both the consumption of isocyanate and the consumption of free amine. After each addition of isocyanate the reaction mixture is stirred for 20 min before aliquot removal for TLC. After the final addition, the reaction mixture is allowed to stir overnight. DMF was removed under reduced pressure and the residue is treated with 10% Na$_2$CO$_3$ solution (50 mL). The resulting suspension is stirred for 10 minutes and then extracted with EtOAc (5×50 mL). The organic layer is washed with water (2×25 mL), brine, dried over Na$_2$SO$_4$ and evaporated under reduced pressure. The residue is dissolved in ether and kept for several hours during which time a crystalline mass will separate out, which will be filtered off, washed with cold ether and dried in air. Additional drying is carried out with a vacuum desiccator overnight to provide the product compound 50-0231:

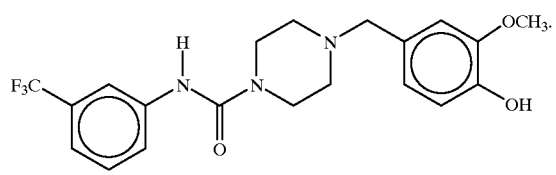

Example 2

Anabolic Ex-Vivo Calvaria Assay

Calvaria from 4–5 day old neonatal CD-1 mice (pregnant mice received from Charles River Laboratories, Wilmington, Mass.) were removed and trimmed with fine-tipped scissors to leave the parietal regions, including the sagittal suture. These trimmed bones were placed singly per well into 6-well cell culture cluster plates (Costar, Pleasanton, Calif.) with 1 ml/well of growth medium containing test compounds or controls. Growth media used was BGJb, 0.1% BSA, 50 μg/ml ascorbic acid. Powdered BGJb (Fitton-Jackson modification; Sigma Chemical Co., St. Louis, Mo.) was dissolved in sterile distilled water (Baxter Healthcare Corp., Deerfield, Ill.); sodium bicarbonate added at 3.5 g/L and pH adjusted to 6.83 and brought to volume. To this was added BSA (Fraction V, Sigma Chemical Co.) at 1 mg/ml, Pen-Strep at 100 U/ml and L-Glutamine at 10 ml/L of a 200 mM stock. The media was sterilized through a 0.22 μm filter. Calvaria were rocked gently (RedRocker™, model PR50-115V, Hoefer, San Francisco, Calif. or Labline Rocking Shaker, model 4635, Labline Instruments, Melrose Park, Ill.) at 37° C. in a 5% CO2 humidified incubator for 24 hours preincubation.

Following preincubation, media was removed and replaced with 1.5 ml/well of growth media containing test compounds (5, 10, 20 and 30 μg/ml) in DMSO (final assay concentration of DMSO less than or equal to 0.1%). In each experiment 10% fetal bovine serum (FBS) was added as a positive control. All control wells contained a final assay concentration of DMSO equal to that present in test compound wells. Four bones were included in each sample group. Bones were incubated on stainless steel grids, either singly in 12-well plates with 1 ml growth media/well, or optionally at 4 bones/grid/well in 6-well plates with 5 ml growth media/well. Bones were incubated for 96 hours. Observations were made of the general appearance, healthiness and number of cells that migrate from the calvaria during the incubation as a possible indication of cell toxicity. Calvaria to be examined histologically were transferred to glass scintillation vials containing 10 ml of cold 10% neutral buffered formalin.

Following fixation, calvariae were decalcified in 5% formic acid containing 5% neutral buffered formalin, washed in running water, dehydrated in an ascending series of ethanol, cleared in xylene, and embedded in paraffin. Five-micron cross-sections were cut at the mid-parietal bone, deparaffinized, and stained with hematoxylin and eosin/ phloxine B/orange G for evaluation of bone changes. Osteoblasts were identified by the strong basophilic cytoplasmic stain, central negative Golgi area, and eccentrically located nucleus. Fibroblasts and osteogenic cells (osteoblast progenitors) on the periosteal surface, which could not be distinguished under the staining method used, were considered as osteogenic/fibroblast-like tissues.

Evaluation of bone formation was made semiqualitatively by examining changes in periosteal tissues (osteogenic/fibroblast-like tissues), osteoblasts and the amount of new bone formed (light orange vs. pinkish/gray pre-existing bone). Arbitrary scores of 0 to 3 are assigned for different levels of bone forming activity.

Score 0: Generally indicated extreme cell toxicity, necrosis and/or cell death.

Score 1: The bone forming activity generally seen in the control cultures. The periosteal surface is covered by one layer of osteoblasts (at about 50% of the bone surface, with the remaining 50% being covered by bone lining cells). A score of "1–" is assigned, if less than 50% of the periosteal surface is covered by osteoblasts due to inhibitory activity or minor toxicity of the agents or compounds being tested (and "1+", if over 50% of the periosteal surface).

Score 2: Shows a moderate increase in bone forming activity. About 20–40% of the periosteal surface is covered by up to two layers of osteoblasts. A score of "2–" is assigned if less than 20% of the periosteal surface is covered by two layers of osteoblasts (and "2+", if over 40% of the periosteal surface).

Score 3: Shows a marked increase in bone forming activity (e.g., stimulation by 10% of fetal bovine serum). More than 20% of the periosteal surface is covered by three layers of osteoblasts. At the same time, the cell appears plump (maximal size exceeds 100 $\mu m^2$). A score of "3–" is assigned if less than 20% of the periosteal surface is covered by three layers of osteoblasts and/or if maximal osteoblast size is less than 100 $\mu m^2$. A score of more than 3 (i.e., "3+") has never been observed.

The compound 50-0231 showed a clear anabolic effect, as indicated by increases in osteoblast number, osteogenic/fibroblast-like tissues (i.e., increased periosteal width), and new bone formation, compared with those in BGJ-treated controls. The maximal effective concentration appears to be between 10–20 $\mu$g/ml (see Table 1).

TABLE 1

| Treatment | Score | Description |
| --- | --- | --- |
| Media control | 1 | 1–2 layers of osteoblasts, thin layer of osteogenic/fibroblastic tissues (i.e., periosteal width) with exception at or near suture lines. |
| 10% Fetal bovine serum Positive control | 3 | 1–3 layers of osteoblasts which appeared plump. Increases in osteogenic/fibroblastic tissues. Increased number of osteoblasts and new bone formation. |
| 50-0231 30 $\mu$g/ml | 1 | Small increase in osteogenic/fibroblastic tissues. Increases in osteoblast number and new bone formation not evident. |
| 50-0231 20 $\mu$g/ml | 2 | 1–3 layers of osteoblasts which appeared plump. Increases in osteogenic/fibroblastic tissues. Increased number of osteoblasts and new bone formation were evident. |
| 50-0231 10 $\mu$g/ml | 2 | Similar to 20 $\mu$g/ml, with additional bone formation. |
| 50-0231 5 $\mu$g/ml | 1+ | Increases in osteogenic/fibroblastic tissues. Increase in number of osteoblasts and new bone formation. |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method to enhance bone formation in a vertebrate animal which method comprises administering to a vertebrate subject in need of such treatment an amount of a compound of formula I:

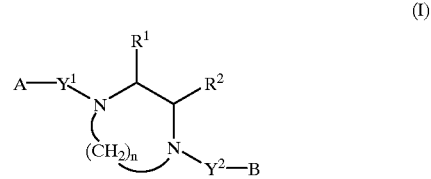

wherein

A and B are each members independently selected from the group consisting of aryl, substituted aryl, carbocyclic ring, substituted carbocyclic ring, heterocyclic ring, substituted heterocyclic ring, and combinations thereof, said combinations being fused or covalently linked and said substituents being selected from the group consisting of halogen, haloalkyl, hydroxy, aryloxy, benzyloxy, alkoxy, haloalkoxy, amino, monoalkylamino, dialkylamino, acyloxy, acyl, unsubstituted alkyl and aryl;

$R^1$ and $R^2$ are each independently selected from the group consisting of hydrogen and alkyl groups having from 1 to 6 carbon atoms, or taken together form a ring selected from the group consisting of saturated or unsaturated five-member rings, saturated or unsaturated six-member rings and saturated or unsaturated seven-member rings;

$Y^1$ and $Y^2$ are each independently a bond or a divalent radical selected from the group consisting of —CH$_2$—, —NHC(O)—, —NRC(O)—, —NHC(S)—, —NRC(S)—, —NHC(=NH)—, —OC(O)—, —C(O)—, and —C(S)—, in which R is a lower alkyl group of from one to six carbon atoms; and n is an integer of from zero to four.

2. A method according to claim 1, wherein said compound has the formula:

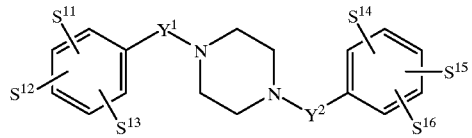

wherein, $Y^1$ and $Y^2$ are each independently a divalent radical selected from the group consisting of —CH$_2$—, —NHC(O)—, —NRC(O)—, —NHC(S)—, —NRC(S)—, —NHC(=NH)—, —OC(O)—, —C(O)—, or —C(S)—, in which R is a lower alkyl group of from one to six carbon atoms; and $S^{11}$, $S^{12}$, $S^{13}$, $S^{14}$, $S^{15}$, and $S^{16}$ are each independently a member selected from the group consisting of hydrogen, halogen, haloalkyl, hydroxy, aryloxy, benzyloxy, alkoxy, haloalkoxy, amino, monoalkylamino, dialkylamino, acyloxy, acyl, unsubstituted alkyl and aryl.

3. A method according to claim 2, wherein $Y^1$ is —NHC(O) or —$CH_2$—, $Y^2$ is —$CH_2$—, and $S^{11}$, $S^{12}$, $S^{13}$, $S^{14}$, $S^{15}$, and $S^{16}$ are each independently members selected from the group consisting of hydrogen, halogen, haloalkyl, hydroxy, alkoxy, haloalkoxy, amino, monoalkylamino or dialkylamino.

4. A method according to claim 2, wherein $S^{11}$, $S^{12}$, $S^{13}$, $S^{14}$, $S^{15}$, and $S^{16}$ are each independently members selected from the group consisting of hydrogen, halogen, trifluoromethyl, hydroxy and methoxy.

5. A method according to claim 2, wherein $Y^1$ is —NHC(O) or —$CH_2$—, $Y^2$ is —$CH_2$—, and $S^{11}$, $S^{12}$, $S^{13}$, $S^{14}$, $S^{15}$, and $S^{16}$ are each independently members selected from the group consisting of hydrogen, halogen, trifluoromethyl, hydroxy and methoxy.

6. The method according to claim 1 wherein said subject is characterized by a condition selected from the group consisting of osteoporosis, bone fracture or deficiency, primary or secondary hyperparathyroidism, periodontal disease or defect, metastatic bone disease, osteolytic bone disease, post-plastic surgery, post-prosthetic joint surgery, and post-dental implantation.

7. The method according to claim 1 which further comprises administering to said subject one or more agents that promote bone growth.

8. The method according to claim 7 wherein said agents are selected from the group consisting of bone morphogenic factors, osteogenic factors, cartilage-derived morphogenic proteins, growth hormones, and differentiating factors.

9. A pharmaceutical composition to enhance bone formation in a vertebrate animal which composition comprises a pharmaceutically acceptable excipient and an amount, effective to promote bone formation, of a compound of the formula:

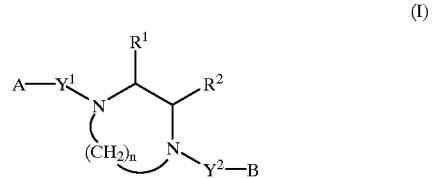

(I)

wherein

A and B are each members independently selected from the group consisting of aryl, substituted aryl, carbocyclic ring, substituted carbocyclic ring, heterocyclic ring, substituted heterocyclic ring, and combinations thereof, said combinations being fused or covalently linked and said substituents being selected from the group consisting of halogen, haloalkyl, hydroxy, aryloxy, benzyloxy, alkoxy, haloalkoxy, amino, monoalkylamino, dialkylamino, acyloxy, acyl, unsubstituted alkyl and aryl;

$R^1$ and $R^2$ are each independently selected from the group consisting of hydrogen and alkyl groups having from 1 to 6 carbon atoms, or taken together form a ring selected from the group consisting of saturated or unsaturated five-member rings, saturated or unsaturated six-member rings and saturated or unsaturated seven-member rings;

$Y^1$ and $Y^2$ are each independently a bond or a divalent radical selected from the group consisting of —$CH_2$—, —NHC(O)—, —NRC(O)—, —NHC(S)—, —NRC(S)—, —NHC(=NH)—, —OC(O)—, —C(O)—, and —C(S)—, in which R is a lower alkyl group of from one to six carbon atoms; and n is an integer of from zero to four.

10. A composition according to claim 9, wherein said compound has the formula:

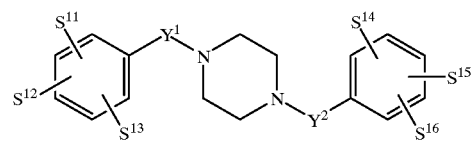

wherein, $Y^1$ and $Y^2$ are each independently a divalent radical selected from the group consisting of —$CH_2$—, —NHC(O)—, —NRC(O)—, —NHC(S)—, —NRC(S)—, —NHC(=NH)—, —OC(O)—, —C(O)—, or —C(S)—, in which R is a lower alkyl group of from one to six carbon atoms; and $S^{11}$, $S^{12}$, $S^{13}$, $S^{14}$, $S^{15}$, and $S^{16}$ are each independently a member selected from the group consisting of hydrogen, halogen, haloalkyl, hydroxy, aryloxy, benzyloxy, alkoxy, haloalkoxy, amino, monoalkylamino, dialkylamino, acyloxy, acyl, unsubstituted alkyl and aryl.

11. A composition according to claim 10, wherein $Y^1$ is —NHC(O) or —$CH_2$—, $Y^2$ is —$CH_2$—, and $S^{11}$, $S^{12}$, $S^{13}$, $S^{14}$, $S^{15}$, and $S^{16}$ are each independently members selected from the group consisting of hydrogen, halogen, haloalkyl, hydroxy, alkoxy, haloalkoxy, amino, monoalkylamino or dialkylamino.

12. A composition according to claim 10, wherein $S^{11}$, $S^{12}$, $S^{13}$, $S^{14}$, $S^{15}$, and $S^{16}$ are each independently members selected from the group consisting of hydrogen, halogen, trifluoromethyl, hydroxy and methoxy.

13. A composition according to claim 10, wherein $Y^1$ is —NHC(O) or —$CH_2$—, $Y^2$ is —$CH_2$—, and $S^{11}$, $S^{12}$, $S^{13}$, $S^{14}$, $S^{15}$, and $S^{16}$ are each independently members selected from the group consisting of hydrogen, halogen, trifluormethyl, hydroxy and methoxy.

* * * * *